(12) United States Patent
Yamamoto et al.

(10) Patent No.: US 11,883,130 B2
(45) Date of Patent: Jan. 30, 2024

(54) DETECTING DEVICE AND MEASURING APPARATUS

(71) Applicant: SEIKO EPSON CORPORATION, Tokyo (JP)

(72) Inventors: Tetsuya Yamamoto, Suwa (JP); Takefumi Fukagawa, Fujimi-Machi (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

(21) Appl. No.: 18/173,758

(22) Filed: Feb. 23, 2023

(65) Prior Publication Data

US 2023/0270339 A1     Aug. 31, 2023

(30) Foreign Application Priority Data

Feb. 28, 2022 (JP) ................. 2022-029120

(51) Int. Cl.
*A61B 5/00* (2006.01)
*A61B 5/024* (2006.01)

(52) U.S. Cl.
CPC ........ *A61B 5/0077* (2013.01); *A61B 5/02438* (2013.01)

(58) Field of Classification Search
CPC ..... A61B 5/024; A61B 5/021; A61B 5/02438; A61B 5/1455; A61B 5/14552; A61B 5/0077; A61B 5/02427; A61B 5/02433; B61B 5/02444

See application file for complete search history.

(56) References Cited

U.S. PATENT DOCUMENTS

| | | | | |
|---|---|---|---|---|
| 10,813,578 | B1* | 10/2020 | Ben Ishay | ............... A61B 5/681 |
| 2008/0287809 | A1* | 11/2008 | Amano | ............. G01N 21/4795 600/476 |
| 2017/0035308 | A1* | 2/2017 | Gulati | ................ G01N 21/4795 |
| 2017/0325698 | A1* | 11/2017 | Allec | ................. A61B 5/14552 |
| 2022/0225945 | A1* | 7/2022 | Eletr | ..................... A61B 5/318 |

FOREIGN PATENT DOCUMENTS

JP          2018149157          9/2018

* cited by examiner

*Primary Examiner* — Lixi C Simpson
(74) *Attorney, Agent, or Firm* — JCIPRNET

(57) ABSTRACT

A detecting device includes a semiconductor substrate, a first light-emitting section provided in a layered manner at the semiconductor substrate and configured to emit first light having a first wavelength band toward a living body, a second light-emitting section provided at the semiconductor substrate in a layered manner and configured to emit second light having a second wavelength band toward the living body, a first light-receiving section provided at the semiconductor substrate and configured to receive light from the living body based on the first light, a second light-receiving section provided at the semiconductor substrate and configured to receive light from the living body based on the second light, and an optical filter provided at the first light-receiving section and configured to transmit light having the first wavelength band and to attenuate light having the second wavelength band. The second wavelength band is longer than the first wavelength band.

8 Claims, 10 Drawing Sheets

DETECTING DEVICE AND MEASURING APPARATUS

The present application is based on, and claims priority from JP Application Serial Number 2022-029120, filed Feb. 28, 2022, the disclosure of which is hereby incorporated by reference herein in its entirety.

BACKGROUND

1. Technical Field

The present disclosure relates to a detecting device and a measuring apparatus.

2. Related Art

Various measurement technologies for non-invasively measuring biological information such as a pulse wave have been known in the related art.

For example, JP-A-2018-149157 discloses a biological information acquisition system including a light source for irradiating the living body, a first light-receiving section for receiving first light corresponding to the concentration of a predetermined substance in the living body, and a second light-receiving section for receiving second light that is not affected by the predetermined substance. An optical filter that permits the passage of the first light and that cuts the second light on a photosensitive surface of the first light-receiving section is provided. An optical filter that permits the passage of the second light and that cuts the first light on a photosensitive surface of the second light-receiving section is provided.

In the biological information acquisition system as described above, it is required to reduce power consumption.

SUMMARY

An aspect of a detecting device according to the present disclosure includes
  a semiconductor substrate,
  a first light-emitting section provided at the semiconductor substrate, the first light-emitting section being configured to emit first light having a first wavelength band toward a living body,
  a second light-emitting section provided at the semiconductor substrate, the second light-emitting section being configured to emit second light having a second wavelength band toward the living body, the second wavelength band being longer than the first wavelength band,
  a first light-receiving section provided at the semiconductor substrate, the first light-receiving section being configured to receive light from the living body based on the first light,
  a second light-receiving section provided at the semiconductor substrate, the second light-receiving section being configured to receive light from the living body based on the second light, and
  an optical filter provided at the first light-receiving section, the optical filter being configured to transmit light having the first wavelength band and to attenuate light having the second wavelength band, wherein
  in view from a perpendicular line direction of the semiconductor substrate,
  the first light-receiving section surrounds the second light-receiving section,
  the first light-emitting section surrounds the first light-receiving section, and
  the second light-emitting section surrounds the first light-emitting section.

An aspect of a measuring apparatus according to the present disclosure includes an aspect of the detecting device, and an information analysis unit configured to identify biological information from a detection signal indicating a detection result from the detecting device.

DESCRIPTION OF EXEMPLARY EMBODIMENTS

A preferred exemplary embodiment of the present disclosure will be described in detail hereinafter with reference to the drawings. Note that the exemplary embodiment, which will be described below, is not intended to unjustly limit the content of the present disclosure as set forth in the claims. In addition, all of the configurations, which will be described below, are not necessarily essential constituent requirements of the present disclosure.

1. Measuring Apparatus

1.1 Overall Configuration

Figure 1:
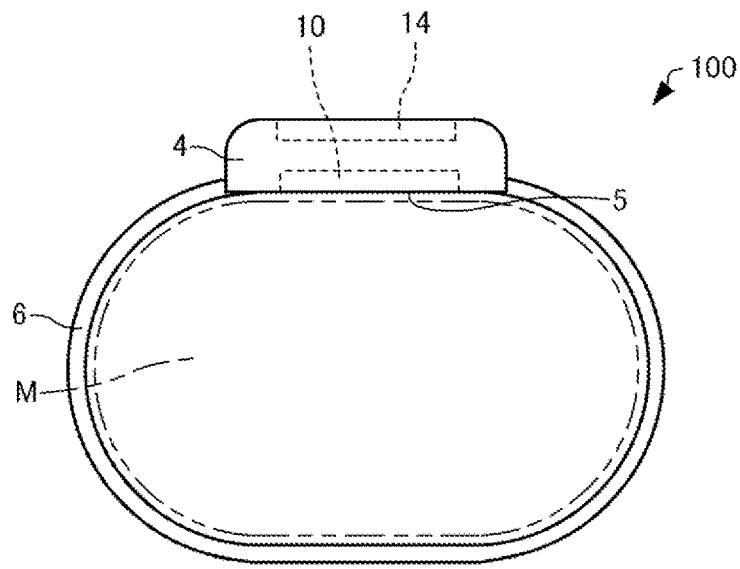
FIG. 1 is a side view schematically illustrating a measuring apparatus according to the present exemplary embodiment.
Figure 2:
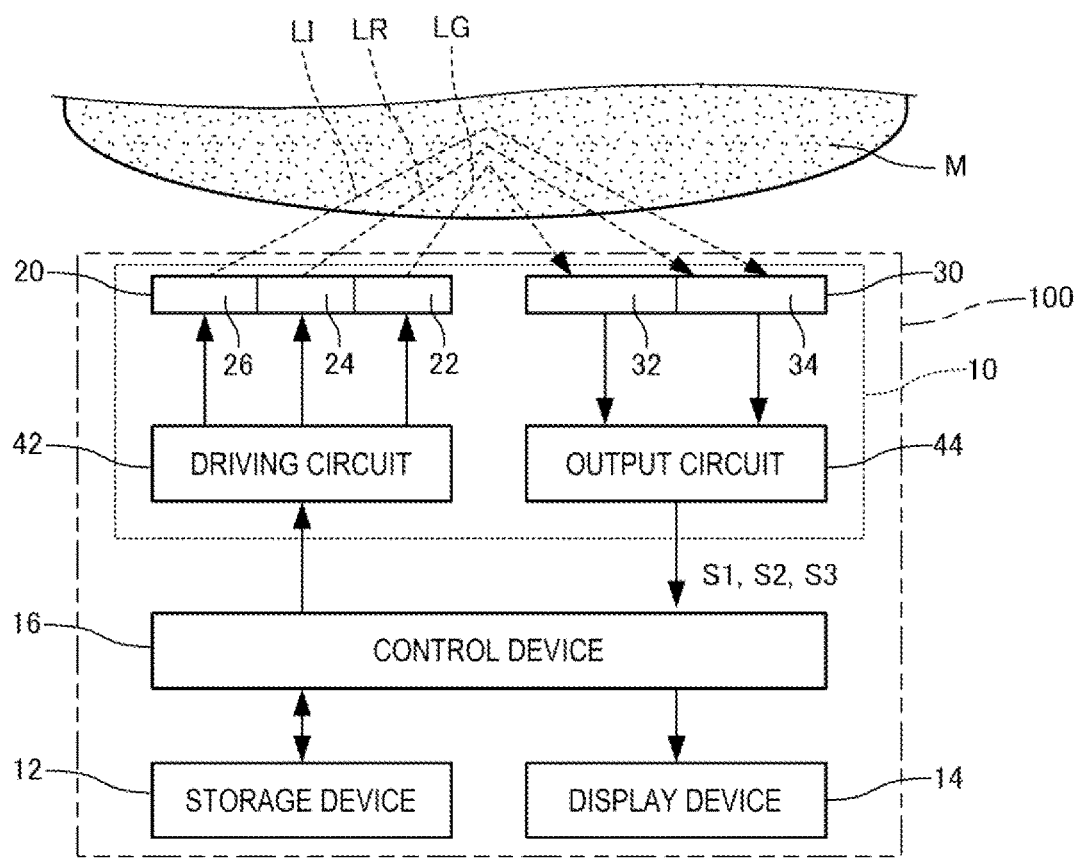
FIG. 2 is a functional block diagram of the measuring apparatus according to the present exemplary embodiment.

First, a measuring apparatus according to a present exemplary embodiment will be described with reference to the accompanying drawings. FIG. 1 is a side view schematically illustrating a measuring apparatus 100 according to the present exemplary embodiment. FIG. 2 is a functional block diagram of the measuring apparatus 100 according to the present exemplary embodiment.

The measuring apparatus 100 is a biometric measuring apparatus that non-invasively measures biological information of a living body M to be measured. Examples of the living body M include, for example, a human body. The living body M is a research subject whose biological information is measured. Examples of a part to be measured of the living body M include the wrist, the fingertips, and the like. In the example illustrated in FIG. 1, the part to be measured of the living body M is the wrist.

As illustrated in FIG. 1, the measuring apparatus 100 includes, for example, a housing 4, and a belt 6. In the illustrated example, the measuring apparatus 100 is a wristwatch-type portable device. The measuring apparatus 100 is mounted on the living body M by winding the belt 6 having a band-like shape on the wrist of the living body M.

The measuring apparatus 100 measures, for example, a pulse wave and a degree of oxygen saturation (SpO2) of the living body M as biological information. The pulse wave indicates a change in volume inside the blood vessel over time in conjunction with the pulsation of the heart. The degree of oxygen saturation indicates a percentage (%) of hemoglobin combining with oxygen with respect to hemoglobin in the blood of the living body M, and is an index for evaluating the respiratory function of the living body M.

As illustrated in FIG. 2, the measuring apparatus 100 includes, for example, the detecting device 10, a storage device 12, a display device 14, and a control device 16.

The detecting device 10 is an optical sensor module that generates detection signals S1, S2, and S3 according to a state of the living body M. The detecting device 10 is provided, for example, at a facing surface 5 of the housing 4 facing the living body M, as illustrated in FIG. 1. The facing surface 5 is a surface that contacts the living body M.

As illustrated in FIG. 2, the detecting device 10 includes, for example, a light-emitting unit 20, a light-receiving unit 30, a driving circuit 42, and an output circuit 44.

The light-emitting unit 20 is configured to emit light. The light-emitting unit 20 includes, for example, a first light-emitting section 22, a second light-emitting section 24, and a third light-emitting section 26. The first light-emitting section 22, the second light-emitting section 24, and the third light-emitting section 26 emit light having wavelengths different from each other to the living body M.

The first light-emitting section 22 emits green light LG having, for example, a green wavelength band from 520 nm to 550 nm toward the living body M. A peak wavelength of the green light LG is, for example, 520 nm.

The second light-emitting section 24 emits red light LR having, for example, a red wavelength band from 600 nm to 800 nm that is longer than the green wavelength band toward the living body M. A peak wavelength of the red light LR is, for example, 660 nm.

The third light-emitting section 26 emits near-infrared light LI having, for example, a near-infrared wavelength band from 800 nm to 1300 nm that is longer than the red wavelength band toward the living body M. A peak wavelength of the near-infrared light LI is, for example, 905 nm. Note that the second light-emitting section 24 may emit the near-infrared light LI, and the third light-emitting section 26 may emit the red light LR.

The light-receiving unit 30 receives light arriving from the living body M after being emitted by the light-emitting unit 20. The light emitted from the light-emitting unit 20 is incident on the living body M, and propagates inside the living body M while being repeatedly reflected and scattered, and then is emitted to the detecting device 10 side, reaching the light-receiving unit 30. The light-receiving unit 30 includes a first light-receiving section 32 and a second light-receiving section 34.

The first light-receiving section 32 receives light in the green wavelength band that has propagated inside the living body M after having been emitted from the first light-emitting section 22 and generates a signal corresponding to an intensity of the received light. In this way, the first light-receiving section 32 receives light in the green wavelength band from the living body M based on the green light LG emitted from the first light-emitting section 22.

The second light-receiving section 34 receives light in the red wavelength band that has propagated inside the living body M after having been emitted from the second light-emitting section 24 and generates a signal corresponding to an intensity of the received light. In this way, the second light-receiving section 34 receives light in the red wavelength band from the living body M based on the red light LR emitted from the second light-emitting section 24. The second light-receiving section 34 receives light in the near-infrared wavelength band that has propagated inside the living body M after having been emitted from the second light-emitting section 24, and generates a signal corresponding to an intensity of the received light. Thus, the second light-receiving section 34 receives light in the near-infrared wavelength band from the living body M based on the near-infrared light LI emitted from the second light-emitting section 24.

The driving circuit 42 causes the first light-emitting section 22, the second light-emitting section 24, and the third light-emitting section 26 to emit light due to the supply of a driving current. The driving circuit 42 periodically causes the light-emitting sections 22, 24, and 26 to emit light in time-division. The driving circuit 42 is constituted by, for example, an integrated circuit (IC).

The output circuit 44 includes, for example, an analog-to-digital converter (A/D converter) that converts signals generated by the first light-receiving section 32 and the second light-receiving section 34 from analog to digital, and an amplifier circuit that amplifies a detection signal after conversion. The output circuit 44 generates the detection signals S1, S2, and S3 for wavelengths different from each other. The output circuit 44 is constituted by, for example, an IC.

Note that one or both of the driving circuit 42 and the output circuit 44 can also be installed as external circuits of the detecting device 10. That is, the detecting device 10 does not need to include the driving circuit 42 and the output circuit 44.

The detection signal S1 generated by the output circuit 44 is a signal indicating an intensity of received light when the first light-receiving section 32 receives the green light LG. The detection signal S2 is a signal indicating an intensity of received light when the second light-receiving section 34 receives the red light LR. The detection signal S3 is a signal indicating an intensity of received light when the second light-receiving section 34 receives the near-infrared light LI. In general, amounts of light absorption by the blood are different between expansion and contraction of the blood vessel. Thus, the detection signals S1, S2, and S3 are pulse wave signals including a pulsating component of the artery inside the living body M, that is, a periodic fluctuation component corresponding to a volume pulse wave.

The storage device 12 is provided inside the housing 4. The storage device 12 is constituted by a random access memory (RAM), a read only memory (ROM), or the like. The storage device 12 stores a program to be executed by the control device 16 and various types of data to be used by the control device 16.

The display device 14 is provided at a surface of the housing 4 at the opposite side to the living body M. The display device 14 is constituted by, for example, a liquid crystal display (LCD), an organic electroluminescence (EL) display, an electrophoretic display (EPD), or the like. The display device 14 displays biological information identified from the detection signals S1, S2, and S3.

The control device 16 is provided inside the housing 4. The control device 16 is an arithmetic processing device constituted by a central processing unit (CPU), a field programmable gate array (FPGA), and the like. Note that the functions of the control device 16 may be configured so as to be dispersed into a plurality of integrated circuits, or may be configured by using a dedicated electronic circuit. Additionally, the control device 16 including the storage device 12 can be implemented by using, for example, an application specific integrated circuit (ASIC), or the like.

The control device 16 identifies biological information of the living body M from the detection signals S1, S2, and S3 generated by the detecting device 10 by executing the program stored in the storage device 12. Specifically, the control device 16 identifies a pulse-to-pulse interval (PPI) of a research subject from the detection signal S1 indicating the intensity of received light of green light LG. The control device 16 also identifies a degree of oxygen saturation of the living body M by analyzing the detection signal S2 indicating the intensity of received light for the red light LR and the detection signal S3 indicating the intensity of received light of the near-infrared light LI.

As described above, in the measuring apparatus 100, the control device 16 functions as an information analysis unit that identifies biological information from the detection signals S1, S2, and S3 indicating the detection results by the detecting device 10. The control device 16 causes the display device 14 to display the biological information identified from the detection signals S1, S2, and S3.

Note that the control device 16 also can notify the user of a measurement result from using a voice output. The control device 16 notifies the user of a warning indicating a possibility of a physical functional trouble when a pulse rate or a degree of oxygen saturation changes to a numerical value out of a predetermined range.

The measuring apparatus 100 as described above is applied to, for example, a smart watch, an activity meter, or the like.

1.2. Detecting Device

1.2.1. Configuration

Figure 3:
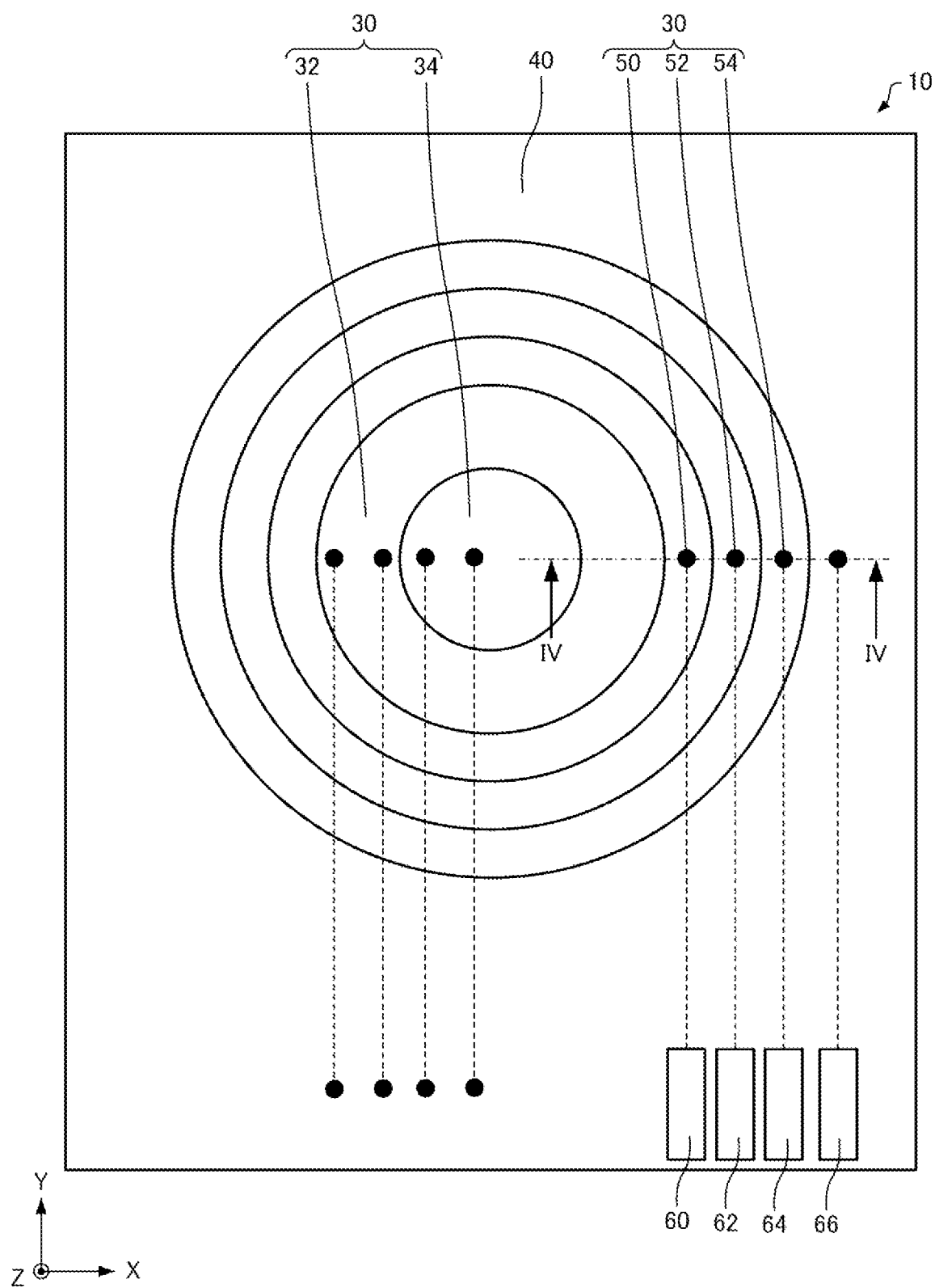
FIG. 3 is a plan view schematically illustrating a detecting device according to the present exemplary embodiment.
Figure 4:
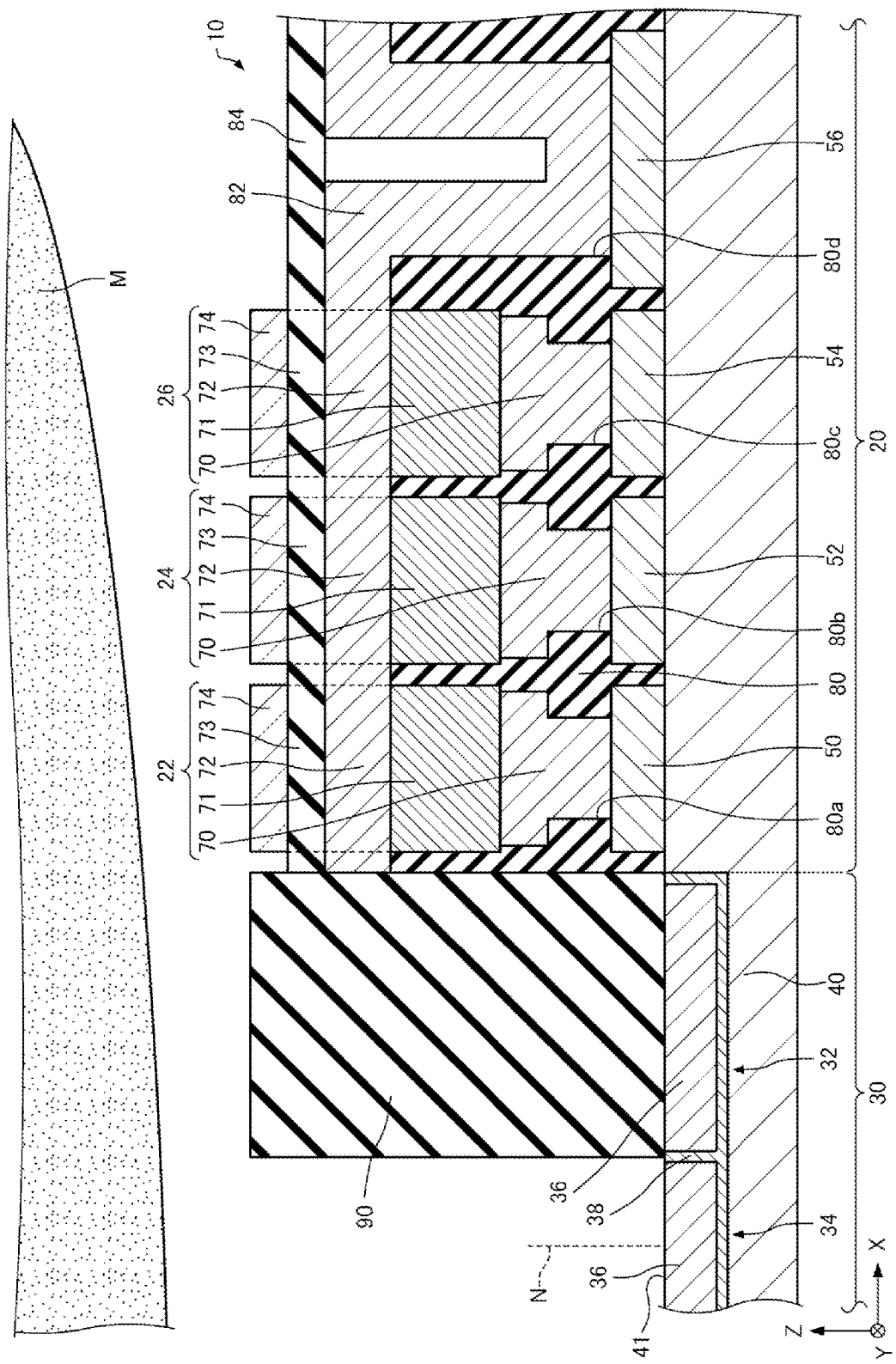
FIG. 4 is a cross-sectional view schematically illustrating the detecting device according to the present exemplary embodiment.

FIG. 3 is a plan view schematically illustrating the detecting device 10. FIG. 4 is a cross-sectional view schematically illustrating the detecting device 10, and corresponds to a part of a IV-IV line in FIG. 3. Note that, in FIG. 3 and FIG. 4, an X-axis, a Y-axis, and a Z-axis are illustrated as three axes orthogonal to each other.

As illustrated in FIG. 3 and FIG. 4, the detecting device 10 includes the light-emitting unit 20, the light-receiving unit 30, and the semiconductor substrate 40. The light-emitting unit 20 includes, for example, the first light-emitting section 22, the second light-emitting section 24, the third light-emitting section 26, pads 60, 62, 64, and 66, an insulating layer 80, a conductive layer 82, and a sealing layer 84. The light-receiving unit 30 includes the first light-receiving section 32, the second light-receiving section 34, and the optical filter 90.

Note that, for convenience, in FIG. 3, members other than the light-emitting sections 22, 24, and 26, the light-receiving sections 32 and 34, the semiconductor substrate 40, and the pads 60, 62, 64, and 66 of the light-emitting unit 20 are omitted.

The semiconductor substrate 40 is, for example, a silicon substrate. The semiconductor substrate 40 includes a main surface 41. The main surface 41 is a surface at the living body M side of the semiconductor substrate 40. For example, the light-emitting sections 22, 24, and 26, and the light-receiving sections 32 and 34 are formed on the main surface 41. In the illustrated example, a perpendicular line N of the main surface 41 of the semiconductor substrate 40 is parallel to the Z-axis. In the following, a state being viewed from the perpendicular line N direction is also referred to as "in plan view".

A first wiring line 50, a second wiring line 52, a third wiring line 54, and a fourth wiring line 56 are provided on the semiconductor substrate 40. The first wiring line 50 couples the first pad 60 and the anode 70 of the first light-emitting section 22. The first wiring line 50 of the light-emitting section 22 is constituted by, for example, a conductive reflective film that causes light emitted from an organic light-emitting layer 71 of the first light-emitting section 22 to reflect in the +Z-axis direction. The second wiring line 52 couples the second pad 62 and the anode 70 of the second light-emitting section 24. The second wiring line 52 of the light-emitting section 24 is constituted by, for example, a conductive reflective film that causes the light emitted from the organic light-emitting layer 71 of the second light-emitting section 24 to reflect in the +Z-axis direction. The third wiring line 54 couples the third pad 64 and the anode 70 of the third light-emitting section 26. The third wiring line 54 of the light-emitting section 26 is constituted by, for example, a conductive reflective film that causes the light emitted from the organic light-emitting layer 71 of the third light-emitting section 26 to reflect in the +Z-axis direction. The fourth wiring line 56 electrically couples the fourth pad 66 and cathodes 72 of the light-emitting sections 22, 24, and 26. Materials of the wiring lines 50, 52, 54, and 56, and the pads 60, 62, 64, and 66 are, for example, an alloy of aluminum and copper, TiN, or a laminate thereof.

As illustrated in FIG. 4, the first light-emitting section 22 including the first wiring line 50 is provided in a layered manner on the semiconductor substrate 40. The second light-emitting section 24 including the second wiring line 52 is provided in a layered manner on the semiconductor substrate 40. The third light-emitting section 26 including the third wiring line 54 is provided in a layered manner on the semiconductor substrate 40.

Each of the first light-emitting section 22, the second light-emitting section 24, and the third light-emitting section 26 include, for example, the anode 70, the organic light-emitting layer 71, the cathode 72, a sealing section 73, and a color filter 74. The light-emitting sections 22, 24, and 26 are constituted by, for example, organic light-emitting diodes.

The anode 70 is one electrode for supplying a current to the organic light-emitting layer 71. In plan view, the anode 70 overlaps the organic light-emitting layer 71. The anode 70 of the first light-emitting section 22 is coupled to the first wiring line 50 through a first contact hole 80a provided in the insulating layer 80. The anode 70 of the second light-emitting section 24 is coupled to the second wiring line 52 through a second contact hole 80b provided in the insulating layer 80. The anode 70 of the third light-emitting section 26 is coupled to the third wiring line 54 through a third contact hole 80c provided in the insulating layer 80. The anode 70 is, for example, a transparent electrode made of indium tin oxide (ITO).

The organic light-emitting layer 71 is provided between the anode 70 and the cathode 72. The organic light-emitting layer 71 emits light by injecting a current by the anode 70 and the cathode 72. Depending on a type of dopant in the organic light-emitting layer 71, the light-emitting sections 22, 24, and 26 can emit light having wavelengths different from each other.

The cathode 72 is the other electrode for supplying a current to the organic light-emitting layer 71. The cathode 72 is provided on the organic light-emitting layer 71. In the illustrated example, the cathodes 72 of the light-emitting sections 22, 24, and 26 are constituted by using a common conductive layer 82. The cathode 72 of the first light-emitting section 22 is a portion of the conductive layer 82 that overlaps the organic light-emitting layer 71 of the first light-emitting section 22 in plan view. The cathode 72 of the second light-emitting section 24 is a portion of the conductive layer 82 that overlaps the organic light-emitting layer 71 of the second light emitting section 24 in plan view. The cathode 72 of the third light-emitting section 26 is a portion of the conductive layer 82 that overlaps the organic light-emitting layer 71 of the third light-emitting section 26 in plan view. The cathode 72 transmits light emitted by the organic light-emitting layer 71. The cathode 72 is, for example, an electrode having optical transparency and made of silver magnesium alloy (AgMg).

The sealing section 73 is provided on the cathode 72. In the illustrated example, the sealing sections 73 of the light-emitting sections 22, 24, and 26 are constituted by the common sealing layer 84. The sealing section 73 of the first light-emitting section 22 is a portion of the sealing layer 84 that overlaps the organic light-emitting layer 71 of the first light-emitting section 22 in plan view. The sealing section 73 of the second light-emitting section 24 is a portion of the sealing layer 84 that overlaps the organic light-emitting layer 71 of the second light-emitting section 24 in plan view. The sealing section 73 of the third light-emitting section 26 is a portion of the sealing layer 84 that overlaps the organic light-emitting layer 71 of the third light-emitting section 26 in plan view. The sealing section 73 transmits light emitted by the organic light-emitting layer 71. The sealing section 73 is made of, for example, silicon oxide, and silicon nitride having good translucency and sealing performance.

The color filter 74 is provided on the sealing section 73. The color filter 74 of the first light-emitting section 22 overlaps the organic light-emitting layer 71 of the first light-emitting section 22 in plan view. The color filter 74 of the first light-emitting section 22 selectively transmits light emitted by the organic light-emitting layer 71 of the first light-emitting section 22. The color filter 74 of the second light-emitting section 24 overlaps the organic light-emitting layer 71 of the second light-emitting section 24 in plan view. The color filter 74 of the second light-emitting section 24 selectively transmits light emitted by the organic light-emitting layer 71 of the second light-emitting section 24. The color filter 74 of the third light-emitting section 26 overlaps the organic light-emitting layer 71 of the third light-emitting section 26 in plan view. The color filter 74 of the third light-emitting section 26 selectively transmits light emitted by the organic light-emitting layer 71 of the third light-emitting section 26.

The shape and size of the color filter 74 are, for example, the same as the shape and size of the organic light-emitting layer 71 in plan view. That is, the shape and size of the color filter 74 of the first light-emitting section 22 are, for example, the same as the shape and size of the organic light-emitting layer 71 of the first light-emitting section 22. The shape and size of the color filter 74 of the second light-emitting section 24 are, for example, the same as the shape and size of the organic light-emitting layer 71 of the second light-emitting section 24. The shape and size of the color filter 74 of the third light-emitting section 26 are, for example, the same as the shape and size of the organic light-emitting layer 71 of the third light-emitting section 26.

Note that, the example in which the organic light-emitting layers 71 are separated from each other in the light-emitting sections 22, 24, and 26, and the organic light-emitting layers 71 emit light having different wavelengths from each other has been described above, but the organic light-emitting layers 71 may be constituted by a common organic light-emitting layer in the light-emitting sections 22, 24, and 26. In this case, the organic light-emitting layer 71 emits white light. By passing the emitted white light through the color filter 74, the light-emitting unit 20 can emit light having different wavelengths from each other. In this case, the organic light-emitting layer 71 of the first light-emitting section 22 is a portion that overlaps the color filter 74 of the first light-emitting section 22 in plan view of the common organic light-emitting layer. The organic light-emitting layer 71 of the second light-emitting section 24 is a portion that overlaps the color filter 74 of the second light-emitting section 24 in plan view of the common organic light-emitting layer. The organic light-emitting layer 71 of the third light-emitting section 26 is a portion that overlaps the color filter 74 of the third light-emitting section 26 in plan view of the common organic light-emitting layer.

The insulating layer 80 is provided on the semiconductor substrate 40. The insulating layer 80 is provided between the organic light-emitting layer 71 of the first light-emitting section 22 and the organic light-emitting layer 71 of the second light-emitting section 24. Furthermore, the insulating layer 80 is provided between the organic light-emitting layer 71 of the second light-emitting section 24 and the organic light-emitting layer 71 of the third light-emitting section 26. The insulating layer 80 is, for example, a silicon oxide layer, a silicon nitride layer, and the like.

The conductive layer 82 is provided on the insulating layer 80. The conductive layer 82 is coupled to the fourth wiring line 56 through a fourth contact hole 80d provided in the insulating layer 80. The portions of the conductive layer 82 corresponding to the light-emitting sections 22, 24, and 26 constitute the cathodes 72. The material of the conductive layer 82 is the same as that of the cathode 72.

The sealing layer 84 is provided on the conductive layer 82. The sealing layer 84 seals the light-emitting sections 22, 24, and 26 through, for example, the conductive layer 82. The portions corresponding to the light-emitting sections 22, 24, and 26 of the sealing layer 84 constitute the sealing sections 73. The material of the sealing layer 84 is the same as that of the sealing sections 73. The sealing layer 84 can reduce moisture entering the organic light-emitting layer 71. The organic light-emitting layer 71 contains an organic material, and thus, is easy to degrade due to moisture.

The first light-receiving section 32 and the second light-receiving section 34 are provided on the semiconductor substrate 40. The first light-receiving section 32 and the second light-receiving section 34 are constituted by, for example, a photodiode (PD), and a phototransistor.

The first light-receiving section 32 and the second light-receiving section 34 include, for example, a first impurity region 36 of a first conductivity type and a second impurity region 38 of a second conductivity type being different from the first conductivity type in the semiconductor substrate 40. The first conductivity type is, for example, a p-type. The second conductivity type is, for example, an n-type.

The first light-receiving section 32 and the second light-receiving section 34 receive light from the living body M based on light emitted by the organic light-emitting layer 71 in the first impurity region 36 of the semiconductor substrate 40. The first impurity region 36 constitutes the light-receiving surfaces of the light-receiving sections 32 and 34. The second impurity region 38 surrounds the first impurity region 36. In the illustrated example, the second impurity region 38 of the first light-receiving section 32 and the second impurity region 38 of the second light-receiving section 34 are common impurity regions. The second impurity region 38 of the first light-receiving section 32 overlaps the first impurity region 36 of the first light-receiving section 32 in plan view. The second impurity region 38 of the second light-receiving section 34 overlaps the first impurity region 36 of the second light-receiving section 34 in plan view.

Note that, although not illustrated, a color filter that selectively transmits light in the green wavelength band may be layered on the first light-receiving section 32. Additionally, a color filter that selectively transmits light in the red wavelength band and light in the near-infrared wavelength band may be layered on the second light-receiving section 34.

The optical filter 90 is provided in a layered manner on the first light-receiving section 32. The optical filter 90 overlaps the first light-receiving section 32 in plan view. The optical filter 90 is not provided on the second light-receiving section 34. The optical filter 90 does not overlap the first light-receiving section 32 in plan view. In the illustrated example, the optical filter 90 is in contact with the insulating layer 80. Also, the optical filter 90 is provided at the inner periphery of the first light-emitting section 22.

The optical filter 90 transmits light having the green wavelength band, and attenuates light having the red wavelength band and light having the near-infrared wavelength band. The optical filter 90 attenuates, for example, light other than light having the green wavelength band. The optical filter 90 selectively transmits, for example, light having the green wavelength band without transmitting light other than light having the green wavelength band.

The optical filter 90 is, for example, a band pass filter, or a low pass filter. For the optical filter 90, a multilayer body in which a plurality of high refractive index layers such as titanium oxide layers, and a plurality of low refractive index layers such as silicon oxide layers are alternately layered is used.

The optical filter 90 may be continuous with the sealing layer 84 and integrally formed with the sealing layer 84. When the optical filter 90 is integrally formed with the sealing layer 84, the number of components of the detecting device 10 can be reduced.

A light shielding wall may be provided between the optical filter 90 and the insulating layer 80. The light shielding wall can shield light being directly incident on the light-receiving sections 32 and 34 from the light-emitting sections 22, 24, and 26 without through the living body M. The light shielding wall may be provided on the semiconductor substrate 40, between the first impurity region 36 of the first light-receiving section 32 and the first impurity region 36 of the second light-receiving section 34 in plan view.

As illustrated in FIG. 3, in plan view, the first light-receiving section 32 surrounds the second light-receiving section 34. The first light-emitting section 22 surrounds the first light-receiving section 32. The second light-emitting section 24 surrounds the first light-emitting section 22. The third light-emitting section 26 surrounds the second light-emitting section 24.

Although illustration is omitted in FIG. 3, as can be seen from FIG. 4, the first impurity region 36 of the first light-receiving section 32 surrounds the first impurity region 36 of the second light-receiving section 34 in plan view. Further, the organic light-emitting layer 71 of the first light-emitting section 22 surrounds the first impurity region 36 of the first light-receiving section 32. The organic light-emitting layer 71 of the second light-emitting section 24 surrounds the organic light-emitting layer 71 of the first light-emitting section 22. The organic light-emitting layer 71 of the third light-emitting section 26 surrounds the organic light-emitting layer 71 of the second light-emitting section 24.

A distance between the first light-emitting section 22 and the first light-receiving section 32 is smaller than a distance between the second light-emitting section 24 and the second light-receiving section 34. A distance between the second light-emitting section 24 and the second light-receiving section 34 is larger than a distance between the third light-emitting section 26 and the second light-receiving section 34.

In the illustrated example, in plan view, the light-emitting sections 22, 24, and 26 have a ring-like shape. The first light-receiving section 32 has a ring-like shape. The second light-receiving section 34 has a circular shape. In plan view, the center position of the first light-emitting section 22, the center position of the second light-emitting section 24, the center position of the third light-emitting section 26, the center position of the first light-receiving section 32, and the center position of the second light-receiving section 34 are the same. In plan view, the semiconductor substrate 40 has a quadrangular shape.

1.2.2. Manufacturing Method

Figure 5:
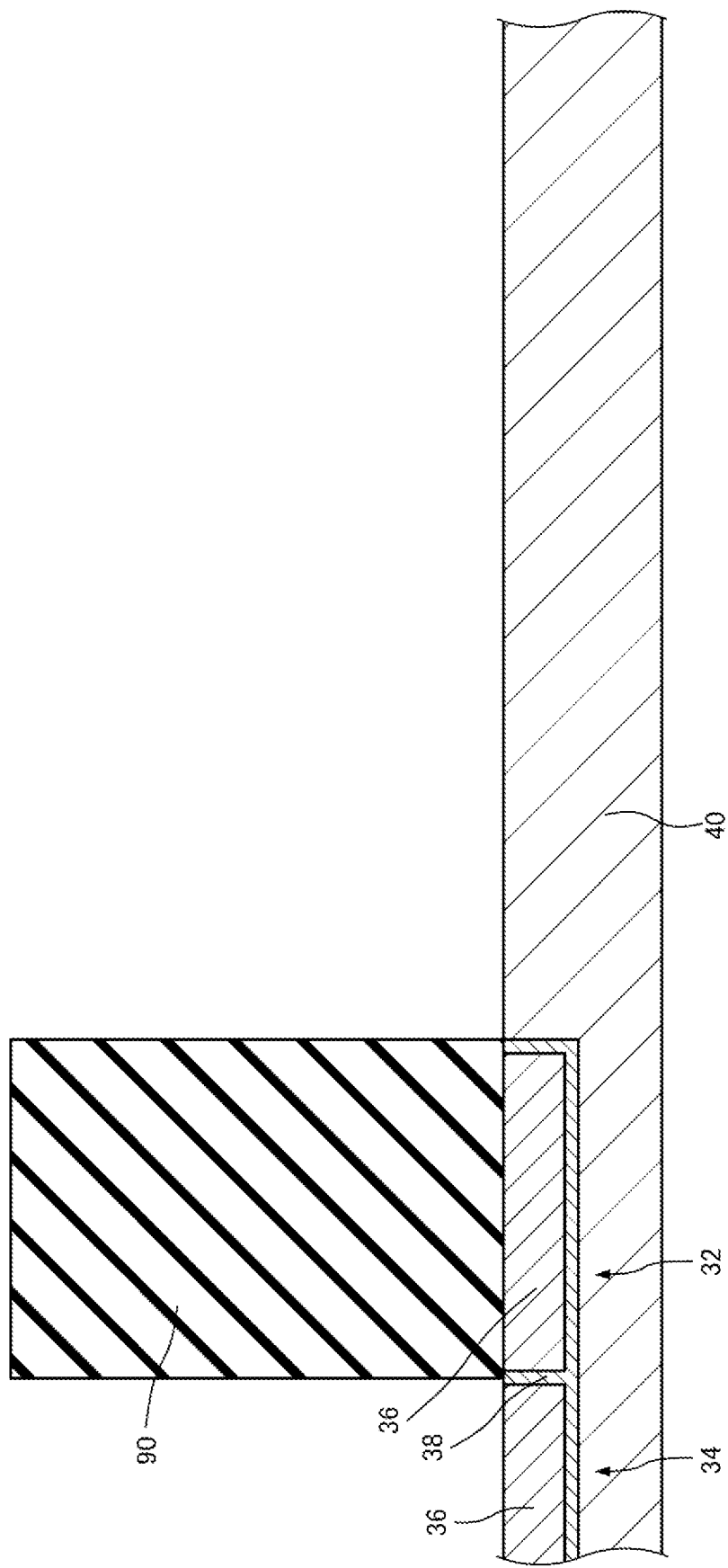
FIG. 5 is a cross-sectional view schematically illustrating a manufacturing process of the detecting device according to the present exemplary embodiment.
Figure 6:
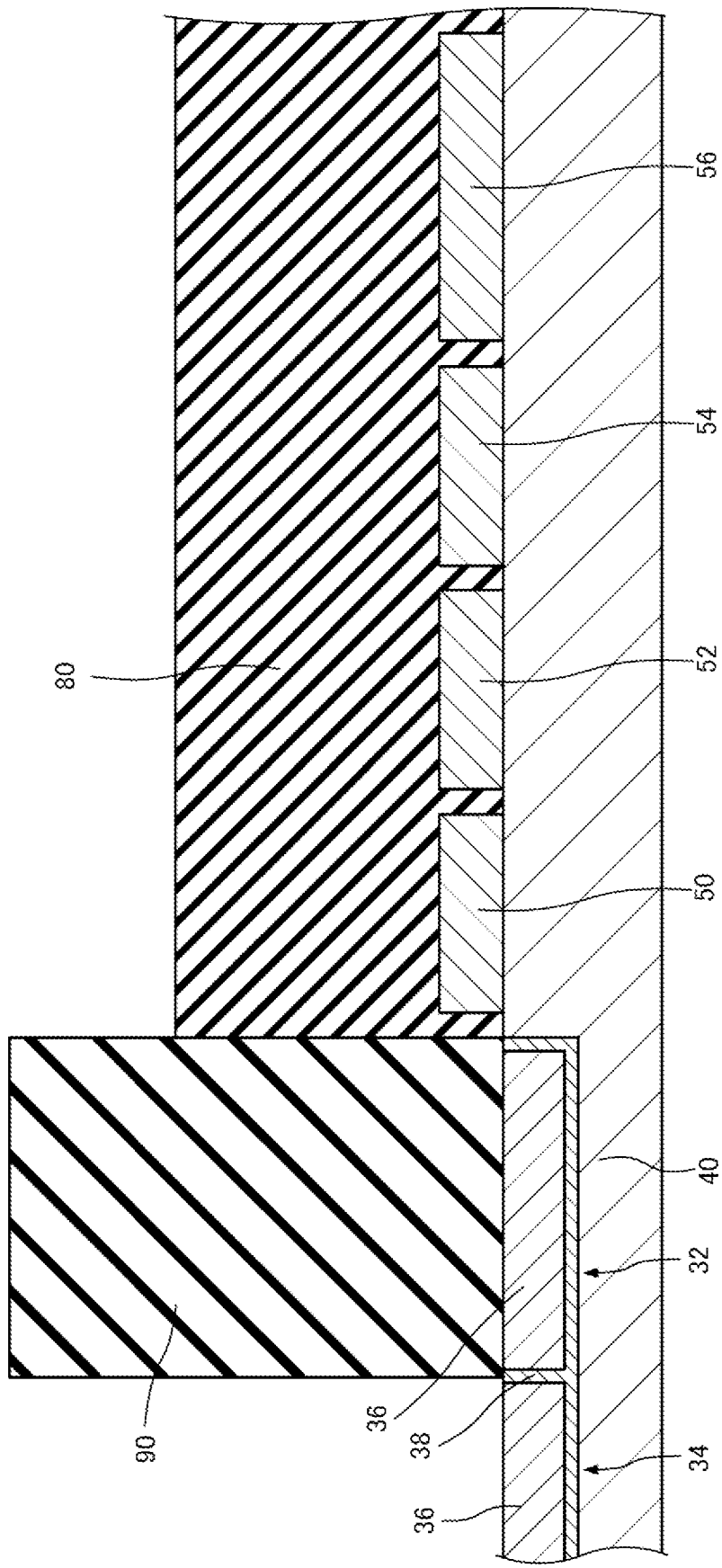
FIG. 6 is a cross-sectional view schematically illustrating the manufacturing process of the detecting device according to the present exemplary embodiment.
Figure 7:
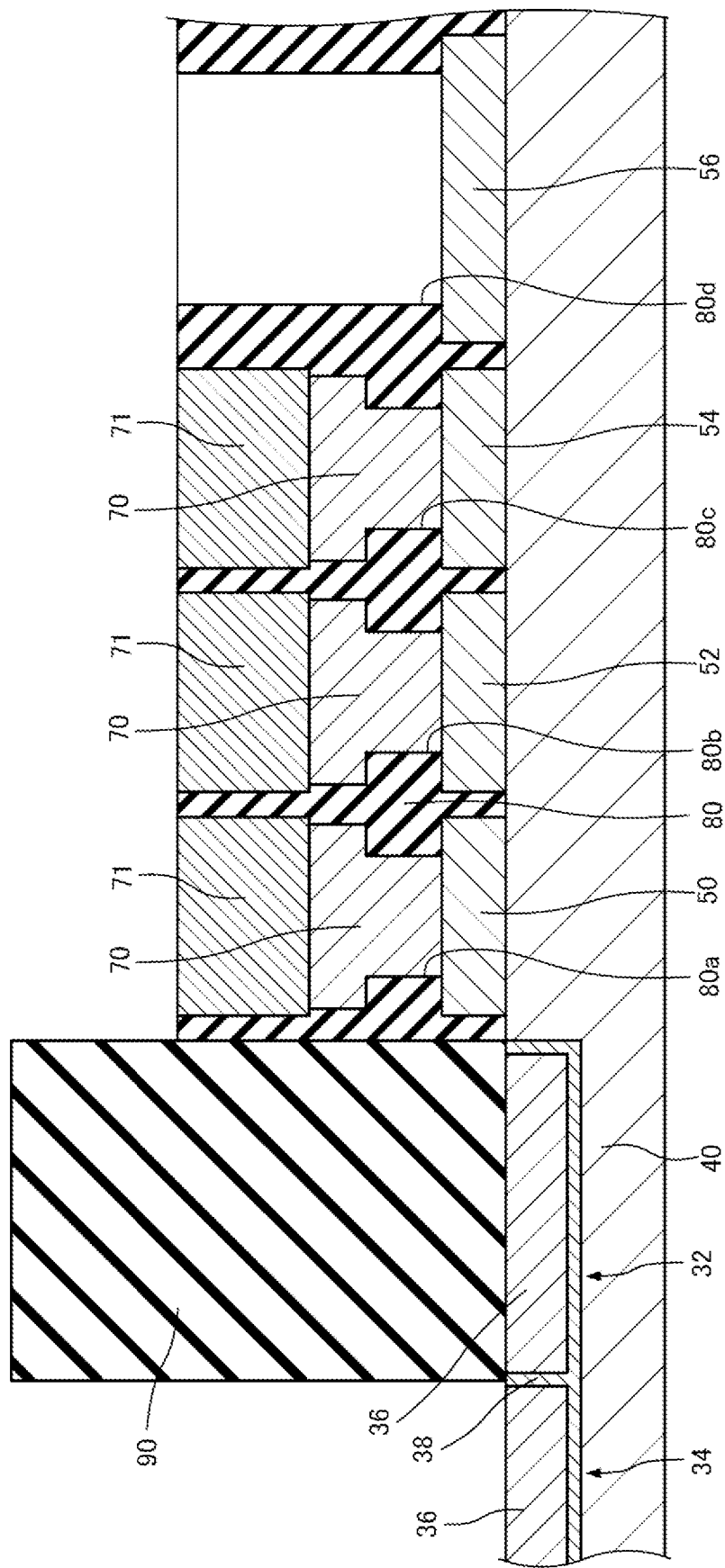
FIG. 7 is a cross-sectional view schematically illustrating the manufacturing process of the detecting device according to the present exemplary embodiment.

Next, a manufacturing method of the detecting device 10 will be described with reference to the drawings. FIG. 5 to FIG. 7 are cross-sectional views schematically illustrating a manufacturing process of the detecting device 10, and correspond to FIG. 4.

FIG. 5 illustrates a state in which the first light-receiving section 32, the second light-receiving section 34, and the optical filter 90 are formed. The semiconductor substrate 40 is implanted with impurities to form the second impurity region 38. Next, impurities are implanted in the second impurity region 38 to form the first impurity region 36. The impurity regions 36 and 38 are formed by, for example, an ion implantation method. This step allows the first light-receiving section 32 and the second light-receiving section 34 to be formed.

Next, the optical filter 90 is formed on the first light-receiving section 32. The optical filter 90 is formed by a chemical vapor deposition (CVD) method, a sputtering method, or the like, for example. When the optical filter 90 is formed by layering a plurality of high refractive index layers and a plurality of low refractive index layers in an alternating manner, the heating treatment is performed, but the light-emitting sections 22, 24, and 26 can be prevented from degrading due to the heating treatment by forming the optical filter 90 before forming the light-emitting sections 22, 24, and 26. In particular, when the light-emitting sections 22, 24, and 26 are constituted by organic light-emitting diodes, the light-emitting sections 22, 24, and 26 are weak to heat, and thus, it is preferable to form the optical filter 90 before forming the light-emitting sections 22, 24, and 26.

As illustrated in FIG. 6, the wiring lines 50, 52, 54, and 56 are formed on the semiconductor substrate 40. In addition, the pads 60, 62, 64, and 66 are formed. The wiring lines 50, 52, 54, and 56, and the pads 60, 62, 64, and 66 are formed by, for example, a sputtering method, a vacuum vapor deposition method, a plating method, or the like.

Next, the insulating layer 80 is formed so as to cover the wiring lines 50, 52, 54, and 56. The insulating layer 80 is formed by, for example, a spin coating method, a CVD method, or the like.

As illustrated in FIG. 7, the insulating layer 80 is patterned to form the contact holes 80*a*, 80*b*, and 80*c*. Patterning is performed, for example, by photolithography and etching.

Next, the anodes 70 are formed on the wiring lines 50, 52, and 54. The anodes 70 are formed by, for example, a sputtering method, a vacuum vapor deposition method, or the like.

Next, the organic light-emitting layer 71 is formed on the anode 70. The organic light-emitting layer 71 is formed by, for example, a vacuum vapor deposition method, a spin coating method, an ink-jet method, or the like.

Next, the insulating layer 80 is patterned to form the fourth contact hole 80*d*. Patterning is performed, for example, by photolithography and etching.

As illustrated in FIG. 4, the conductive layer 82 is formed on the insulating layer 80, on the organic light-emitting layer 71, and on the fourth wiring line 56. The conductive layer 82 is formed by, for example, a sputtering method, a vacuum vapor deposition method, or the like.

Next, the sealing layer 84 is formed on the conductive layer 82. The sealing layer 84 is formed, for example, by a CVD method.

Next, the color filter 74 is formed on the sealing layer 84. The color filter 74 is formed by, for example, a CVD method, a sputtering method, or the like. According to this step, the light-emitting sections 22, 24, and 26 can be formed.

The detecting device 10 can be manufactured by the above steps.

As described above, the light-emitting sections 22, 24, and 26, and the light-receiving sections 32 and 34 are manufactured by a semiconductor process. According to this, as compared to the case where the light-emitting section and the light-receiving section are mounted on the substrate, clearance for implementation is not necessary, and thus, the distance between the first light-emitting section 22 and the first light-receiving section 32 can be reduced, for example. Thus, miniaturization of the detecting device 10 can be achieved.

1.2.3. Actions and Effects

The detecting device 10 includes the semiconductor substrate 40, the first light-emitting section 22 provided in a layered manner at the semiconductor substrate 40, the first light-emitting section 22 being configured to emit the green light LG as the first light having the first wavelength band toward the living body M, the second light-emitting section 24 provided in a layered manner at the semiconductor substrate 40, the second light-emitting section 24 being configured to emit the red light LR as the second light having the second wavelength band longer than the first wavelength band toward the living body M, the first light-receiving section 32 provided at the semiconductor substrate 40, the first light-receiving section 32 being configured to receive light from the living body M based on the green light LG, the second light-receiving section 34 provided at the semiconductor substrate 40, the second light-receiving section 34 being configured to receive light from the living body M based on the red light LR, and the optical filter 90 provided at the first light-receiving section 32, the optical filter 90 being configured to transmit light having the first wavelength band, the optical filter 90 being configured to attenuate light having the second wavelength band. In view from the perpendicular line N direction of the semiconductor substrate 40, the first light-receiving section 32 surrounds the second light-receiving section 34, the first light-emitting section 22 surrounds the first light-receiving section 32, and the second light-emitting section 24 surrounds the first light-emitting section 22.

Figure 8:
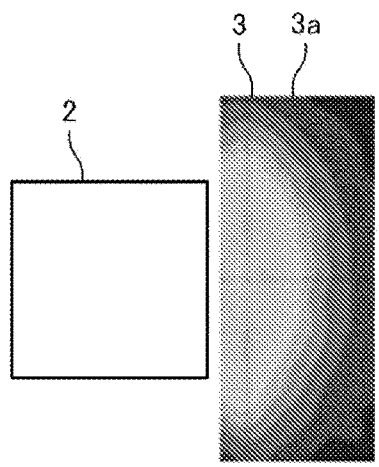
FIG. 8 is a simulation result of an intensity distribution of light emitted from the living body to a light-receiving surface of a light-receiving section when green light is emitted from a light-emitting section.

Here, FIG. 8 is a simulation result of an intensity distribution of light emitted from the living body to the light-receiving surface 3*a* of the light-receiving section 3 when the green light is emitted from the light-emitting section 2. The simulation was performed by using ray tracing software. In FIG. 8, in an intensity distribution of light on the light-receiving surface 3*a*, the whiter a portion is, the larger the intensity is, and the darker a portion is, the smaller the intensity is.

As illustrated in FIG. 8, when the green light LG is emitted from the light-emitting section 2, the intensity of light is locally increased at a portion closer to the light-emitting section 2 on the light-receiving surface 3*a*. In contrast, when the red light LR or the near-infrared light LI is emitted from the light-emitting section 2, the uniformity of the intensity of light is high on the entire surface of the light-receiving surface 3*a*, compared to the case where the green light is emitted.

Figure 9:
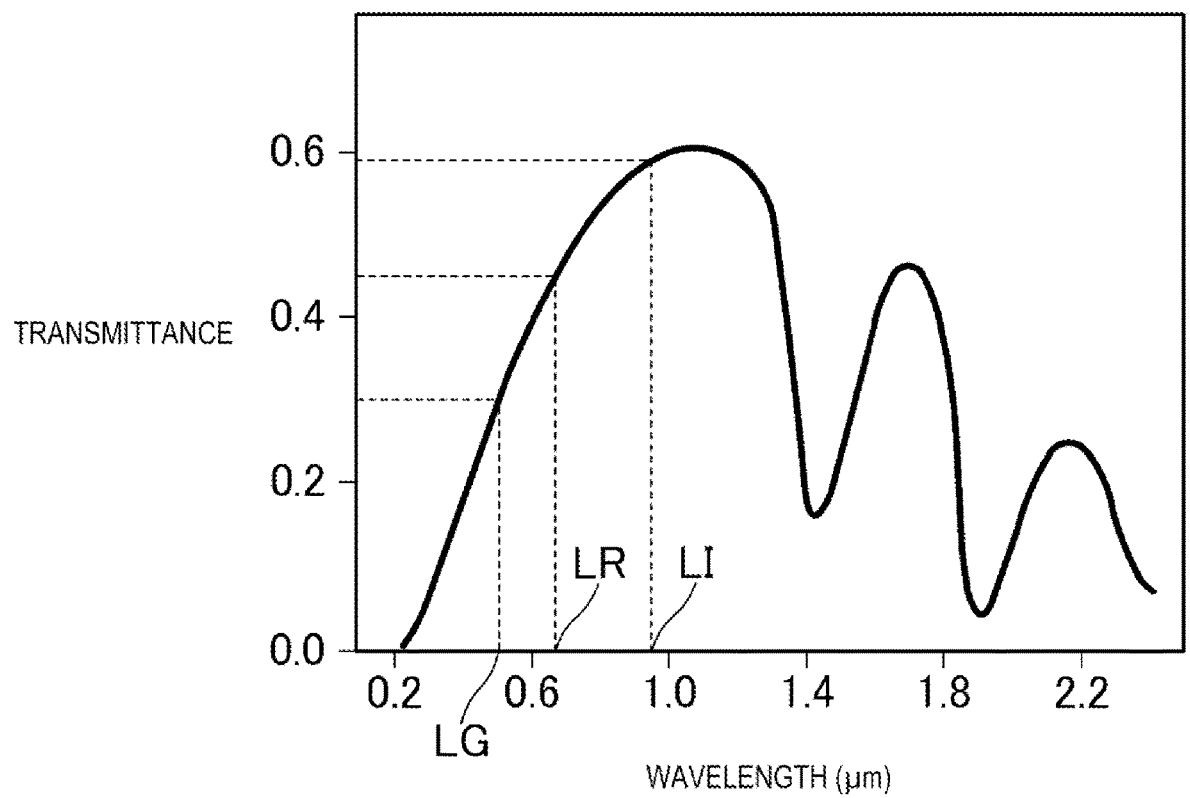
FIG. 9 is a graph illustrating a transmission spectrum of the skin.

FIG. 9 is a graph illustrating a transmission spectrum of the skin. In FIG. 9, the horizontal axis represents a wavelength of light and the vertical axis represents a transmittance. FIG. 9 illustrates a transmission spectrum when a thickness of the skin is 0.43 mm as an example.

As illustrated in FIG. 9, the transmittance when the green light LG is incident on the skin is approximately 30%. The transmittance when the red light LR is incident on the skin is equal to or more than 50% and equal to or less than 60%. The transmittance when the near-infrared light LI is incident on the skin is approximately 60%.

The green light LG has a small transmittance to the living body, compared to the red light LR and the near-infrared light LI as described above. Thus, the green light LG does not reach a deep point of the living body. As a result, it is assumed that the green light LG can propagate in the living body only at a short distance, and the green light LG is locally incident on the vicinity of the light-emitting section 2, as illustrated in FIG. 8.

On the other hand, the red light LR and the near-infrared light LI have a larger transmittance to the living body than that of the green light LG. Thus, the red light LR and the near-infrared light LI reach a deep point of the living body. Due to this, the red light LR and the near-infrared light LI can propagate in the living body at a long distance, and thus, it is assumed that the red light LR and the near-infrared light LI are incident on the entire surface of the light-receiving surface 3a with high uniformity. Note that although FIG. 9 illustrates the case where a thickness of the skin is 0.43 mm as an example, also in the case where the thickness of the skin is different, the red light LR and the near-infrared light LI have a larger transmittance to the living body than that of the green light LG.

As described above, in the detecting device 10, the first light-receiving section 32 that receives light in the green wavelength band surrounds the second light-receiving section 34 that receives light in the red wavelength band, the first light-emitting section 22 that emits the green light LG surrounds the first light-receiving section 32, and the second light-emitting section 24 that emits the red light LR surrounds the first light-emitting section 22. Thus, in the detecting device 10, light in the green wavelength band incident on the first light-receiving section 32 can be increased compared to a case where the positions of the first light-emitting section and the second light-emitting section are opposite to each other, for example. Thus, even when an amount of light emission of the first light-emitting section 22 is suppressed, the light in the green wavelength band can be sufficiently received in the first light-receiving section 32. As a result, power consumption can be reduced.

Furthermore, in the detecting device 10, the second light-receiving section 34 can reduce light having the first wavelength band incident on the second light-receiving section 34 even when the optical filter is not provided in the second light-receiving section 34, and can cause the light having the first wavelength band to be efficiently incident on the first light-receiving section 32. Thus, the detecting device 10 has high utilization efficiency of light.

Furthermore, in the detecting device 10, the optical filter does not need to be provided in the second light-receiving section 34, and thus, the number of components can be reduced. With this configuration, the cost can be reduced.

In the detecting device 10, the first light-emitting section 22 and the second light-emitting section 24 are constituted by an organic light-emitting diode. Thus, in the detecting device 10, degrees of freedom of the shapes and sizes of the first light-emitting section 22 and the second light-emitting section 24 can be increased in plan view compared to a case where the first light-emitting section and the second light-emitting section are light emitting diodes (LEDs) including a light-emitting layer made of a semiconductor material. Thus, in plan view, the first light-emitting section 22 surrounding the first light-receiving section 32 and the second light-emitting section 24 surrounding the first light-emitting section 22 can be easily formed. Furthermore, in plan view, the detecting device 10 can be easily formed compared to a case where a detecting device including a light-receiving section surrounding a light-emitting section is formed.

In the detecting device 10, the optical filter 90 is a band pass filter. Thus, in the detecting device 10, the optical filter 90 can selectively transmit light having the first wavelength band.

In the detecting device 10, the first wavelength band is a green wavelength band. Thus, the detecting device 10 can detect the pulse wave.

In the detecting device 10, the second wavelength band is a red wavelength band or a near-infrared wavelength band. Thus, the degree of oxygen saturation can be detected in the detecting device 10.

2. Modified Examples of Detecting Device 2.1 First Modified Example

Figure 10:
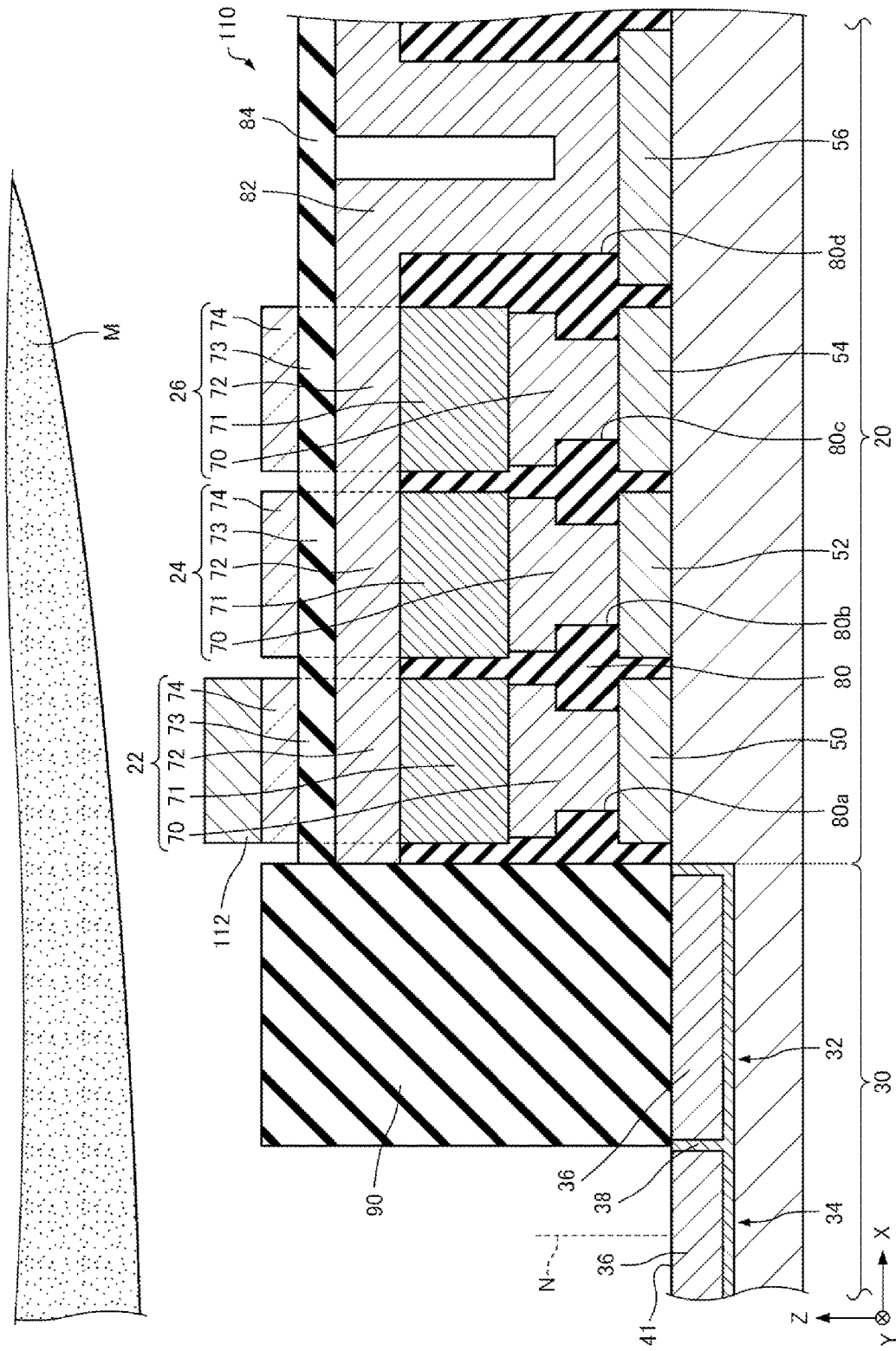
FIG. 10 is a cross-sectional view schematically illustrating a detecting device according to a first modified example of the present exemplary embodiment.

Next, a detecting device according to a first modified example of the present exemplary embodiment will be described in detail with reference to the appended drawings. FIG. 10 is a cross-sectional view schematically illustrating a detecting device 110 according to the first modified example of the present exemplary embodiment.

Hereinafter, in the detecting device 110 according to the first modified example of the present exemplary embodiment, members having functions similar to those of the constituent elements of the detecting device 10 according to the present exemplary embodiment described above are denoted by the same reference signs, and the detailed description thereof is omitted. This is similar in the detecting devices according to second and third modified examples of the present exemplary embodiment, which will be described below.

As illustrated in FIG. 10, the detecting device 110 differs from the detecting device 10 described above in that the detecting device 110 includes an emission angle limiting section 112.

The emission angle limiting section 112 is provided on the color filter 74 of the first light-emitting section 22. The green light LG emitted from the first light-emitting section 22 passes through the emission angle limiting section 112, and is incident on the living body M. For example, a microlens, a microcavity, and a black matrix are used as the emission angle limiting section 112.

The emission angle limiting section 112 limits an emission angle of the green light LG emitted from the first light-emitting section 22. Specifically, the emission angle limiting section 112 narrows the emission angle of the green light LG emitted from the first light-emitting section 22. Thus, the green light LG emitted from the first light-emitting section 22 has directivity. In the illustrated example, the detecting device 110 does not include an emission angle limiting section that limits an emission angle of the red light LR emitted from the second light-emitting section 24, and an emission angle limiting section that limits an emission angle of the near-infrared light LI emitted from the third light-emitting section 26.

Note that a position of the emission angle limiting section 112 is not particularly limited as long as the emission angle of the green light LG emitted from the first light-emitting section 22 can be limited, and may be provided between the color filter 74 and the sealing section 73 of the first light-emitting section 22, and may be provided between the sealing section 73 and the cathode 72 of the first light-emitting section 22, for example.

The detecting device 110 includes the emission angle limiting section 112 that limits the emission angle of the green light LG. Thus, in the detecting device 110, green light being directly incident on the first light-receiving section 32 from the first light-emitting section 22 without through the living body M can be reduced. Thus, the first light-receiving section 32 can have a high signal-to-noise (SN) ratio. Thus, the first light-receiving section 32 can receive light from the living body M with high accuracy, and thus, can suppress the amount of light emission of the first light-emitting section 22. As a result, power consumption can be reduced. The first light-emitting section 22 is closer to the first light-receiving section 32 than the second light-emitting section 24, so that in particular, the emission angle limiting section 112 that limits the emission angle of the green light LG is effective.

2.2. Second Modified Example

Figure 11:
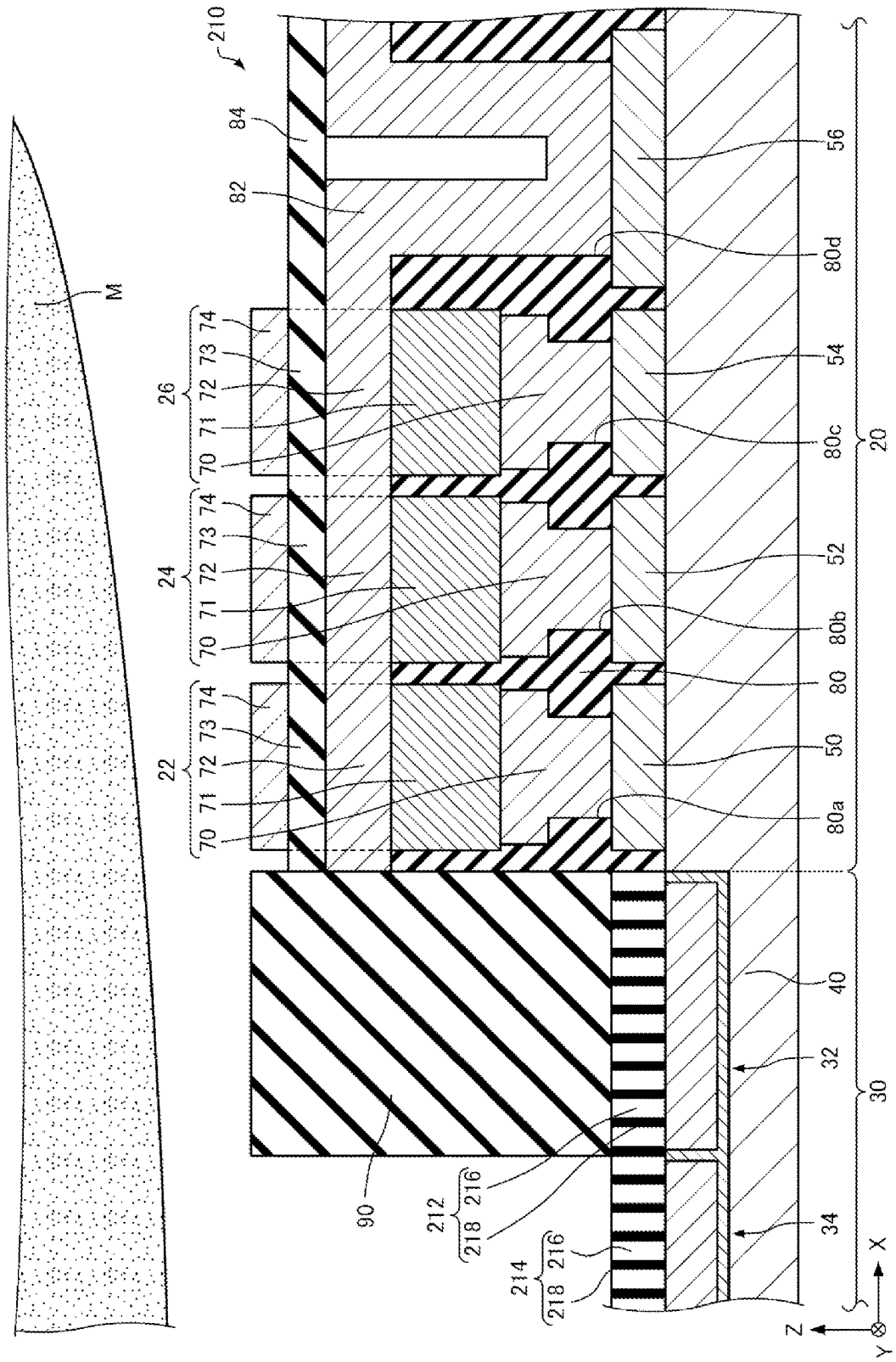
FIG. 11 is a cross-sectional view schematically illustrating a detecting device according to a second modified example of the present exemplary embodiment.

Next, a detecting device according to a second modified example of the present exemplary embodiment will be described with reference to the drawings. FIG. 11 is a cross-sectional view schematically illustrating a detecting device 210 according to a second modified example of the present exemplary embodiment.

As illustrated in FIG. 11, the detecting device 210 differs from the detecting device 10 described above in that the detecting device 210 includes a first angle limiting filter 212 and a second angle limiting filter 214.

The first angle limiting filter 212 is provided on the first light-receiving section 32. The first angle limiting filter 212 is provided between the first light-receiving section 32 and the optical filter 90. Note that although not illustrated, the first angle limiting filter 212 may be provided on the optical filter 90. The second angle limiting filter 214 is provided on the second light-receiving section 34.

The first angle limiting filter 212 and the second angle limiting filter 214 include, for example, a light-transmitting layer 216 and a plug 218 embedded in the light-transmitting layer 216. The light-transmitting layer 216 is, for example, a silicon oxide layer. The plug 218 is constituted by, for example, a light-shielding material such as tungsten.

The light-transmitting layer 216 forms an optical path for guiding light to the light-receiving sections 32 and 34. The plug 218 limits an incident angle of light passing through the light-transmitting layer 216. That is, when light being incident on the light-transmitting layer 216 is tilted more than a predetermined angle with respect to the optical path, the incident light hits the plug 218, and a part of the light is absorbed by the plug 218, and the rest thereof is reflected. Then, repeating reflection of the light while the light is passing through the optical path makes the intensity of reflected light weaker. As a result, the first angle limiting filter 212 can limit an incident angle of light being incident on the first light-receiving section 32. Furthermore, the second angle limiting filter 214 can limit an incident angle of light being incident on the second light-receiving section 34.

Note that the first angle limiting filter 212 may be configured to transmit light in a first incident angle range, and may be configured to attenuate light being incident at an angle smaller than the first incident angle range and light being incident at an angle larger than the first incident angle range. The second angle limiting filter 214 may be configured to transmit light in a second incident angle range and may be configured to attenuate light being incident at an angle smaller than the second incident angle range and light being incident at an angle larger than the second incident angle range. The second incident angle range may be the same as the first incident angle range, or may be different.

The detecting device 210 includes a first angle limiting filter 212 that limits an incident angle of light being incident on the first light-receiving section 32, and a second angle limiting filter 214 that limits an incident angle of light being incident on the second light-receiving section 34. Thus, in the detecting device 210, an incidence of light other than light from the living body M can be suppressed on the light-receiving sections 32 and 34. Because of this, the light-receiving sections 32 and 34 can have a high SN ratio. Thus, the light-receiving sections 32 and 34 can receive light from the living body M with high accuracy, and thus, can suppress the amounts of light emission of the light-emitting sections 22, 24, and 26. As a result, power consumption can be reduced. Examples of light that is not light from the living body M include sunlight, light of a fluorescent lamp in a room where the detecting device 210 is disposed, light being directly incident from the light-emitting sections 22, 24, and 26, and the like.

2.3. Third Modified Example

Figure 12:
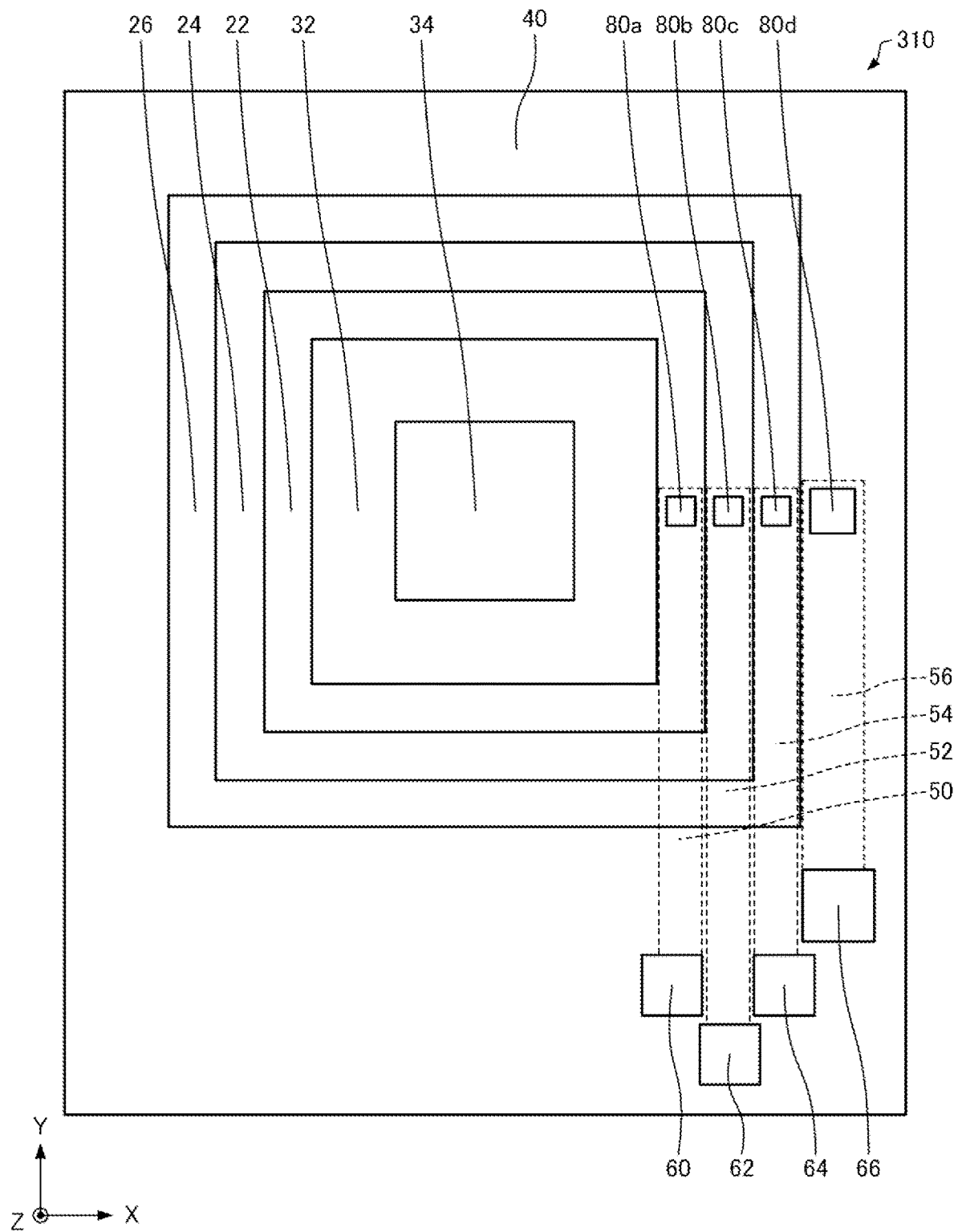
FIG. 12 is a plan view schematically illustrating a detecting device according to a third modified example of the present exemplary embodiment.

Next, a detecting device according to a third modified example of the present exemplary embodiment will be described in detail with reference to the appended drawings. FIG. 12 is a plan view schematically illustrating a detecting device 310 according to the third modified example of the present exemplary embodiment.

In the detecting device 10 described above, as illustrated in FIG. 3, the second light-receiving section 34 has a circular shape in plan view.

In contrast, in the detecting device 310, as illustrated in FIG. 12, the second light-receiving section 34 has a quadrangular shape in plan view. In the illustrated example, the second light-receiving section 34 has a square shape. The first light-receiving section 32 has a shape surrounding the second light-receiving section 34 along the shape of the second light-receiving section 34. The first light-emitting section 22 has a shape surrounding the first light-receiving section 32 along the shape of the first light-receiving section 32. The second light-emitting section 24 has a shape surrounding the first light-emitting section 22 along the shape of the first light-emitting section 22. The third light-emitting section 26 has a shape surrounding the second light-emitting section 24 along the shape of the second light-emitting section 24.

The exemplary embodiment and the modified examples described above are merely examples and are not limited thereto. For example, each of the exemplary embodiment and the modified examples can be combined as appropriate.

The present disclosure includes configurations that are substantially identical to those described in the exemplary embodiment, for example, a configuration having the same functions, methods, and results, or a configuration having the same purposes, and effects. Furthermore, the present disclosure includes a configuration in which a non-essential portion of the configuration described in the exemplary embodiment is replaced. The present disclosure also includes a configuration that can achieve the same effects or the same objects as those of the configuration described in the exemplary embodiment. In addition, the present disclosure includes configurations obtained by adding known techniques to the configuration described in the exemplary embodiment.

The following contents are derived from the above-described exemplary embodiment and modified examples.

A semiconductor substrate,
  a first light-emitting section provided at the semiconductor substrate in a layered manner, the first light-emitting section being configured to emit first light having a first wavelength band toward a living body,
  a second light-emitting section provided at the semiconductor substrate in a layered manner and configured to emit second light having a second wavelength band toward the living body, the second wavelength band being longer than the first wavelength band,
  a first light-receiving section provided at the semiconductor substrate and configured to receive light from the living body based on the first light,
  a second light-receiving section provided at the semiconductor substrate and configured to receive light from the living body based on the second light; and
  an optical filter provided at the first light-receiving section and configured to transmit light having the first wavelength band and to attenuate light having the second wavelength band, are provided.

In view from a perpendicular line direction of the semiconductor substrate,
the first light-receiving section surrounds the second light-receiving section,
the first light-emitting section surrounds the first light-receiving section, and
the second light-emitting section surrounds the first light-emitting section.

According to this detecting device, power consumption can be reduced.

In one aspect of the detecting device,
each of the first light-emitting section and the second light-emitting section may be constituted by an organic light-emitting diode.

According to this detecting device, degrees of freedom in shapes and sizes of the first light-emitting section and the second light-emitting section can be increased.

In one aspect of the detecting device,
the optical filter may be a band pass filter.

According to this detecting device, the optical filter can selectively transmit light having a first wavelength band.

In one aspect of the detecting device, an emission angle limiting section configured to limit an emission angle of the first light may be included.

According to this detecting device, light being directly incident from the first light-emitting section on the first light-receiving section without through the living body can be reduced.

In one aspect of the detecting device, a first angle limiting filter configured to limit an incident angle of light being incident on the first light-receiving section, and
a second angle limiting filter configured to limit an incident angle of light being incident on the second light-receiving section may be included.

According to this detecting device, an incidence of light other than light from the living body M on the first light-receiving section and the second light-receiving section can be suppressed.

In one aspect of the detecting device, the first wavelength band may be a green wavelength band.

According to this detecting device, a pulse wave can be detected.

In one aspect of the detecting device, the second wavelength band may be a red wavelength band or a near-infrared wavelength band.

According to this detecting device, a degree of oxygen saturation can be detected.

One aspect of a measuring apparatus includes
the detecting device, and
an information analysis unit configured to identify biological information from a detection signal indicating a detection result from the detecting device.

What is claimed is:

1. A detecting device, comprising:
a semiconductor substrate;
a first light-emitting section provided at the semiconductor substrate, the first light-emitting section being configured to emit first light having a first wavelength band toward a living body;
a second light-emitting section provided at the semiconductor substrate, the second light-emitting section being configured to emit second light having a second wavelength band toward the living body, the second wavelength band being longer than the first wavelength band;
a first light-receiving section provided at the semiconductor substrate, the first light-receiving section being configured to receive light from the living body based on the first light;
a second light-receiving section provided at the semiconductor substrate, the second light-receiving section being configured to receive light from the living body based on the second light; and
an optical filter provided at the first light-receiving section, the optical filter being configured to transmit light having the first wavelength band and to attenuate light having the second wavelength band, wherein
in view from a perpendicular line direction of the semiconductor substrate,
the first light-receiving section surrounds the second light-receiving section,
the first light-emitting section surrounds the first light-receiving section, and
the second light-emitting section surrounds the first light-emitting section.

2. The detecting device according to claim 1, wherein
each of the first light-emitting section and the second light-emitting section are constituted by an organic light-emitting diode.

3. The detecting device according to claim 1, wherein
the optical filter is a band pass filter.

4. The detecting device according to claim 1, further comprising:
an emission angle limiting section configured to limit an emission angle of the first light.

5. The detecting device according to claim 1, further comprising:
a first angle limiting filter configured to limit an incident angle of light being incident on the first light-receiving section; and
a second angle limiting filter configured to limit an incident angle of light being incident on the second light-receiving section.

6. The detecting device according to claim 1, wherein
the first wavelength band is a green wavelength band.

7. The detecting device according to claim 1, wherein
the second wavelength band is a red wavelength band or a near-infrared wavelength band.

8. A measuring apparatus, comprising:
the detecting device according to claim 1; and
an information analysis unit configured to identify biological information from a detection signal indicating a detection result from the detecting device.

* * * * *